United States Patent [19]
Diebel et al.

[11] 4,078,005
[45] Mar. 7, 1978

[54] PROCESS FOR THE PRODUCTION OF ALKOXYTETRABROMOCTANES

[75] Inventors: Klaus Diebel; Manfred Schröder, both of Marl, Germany

[73] Assignee: Chemische Werke Huels Aktiengesellschaft, Marl, Germany

[21] Appl. No.: 647,155

[22] Filed: Jan. 7, 1976

[30] Foreign Application Priority Data

Jan. 10, 1975    Germany ............................. 2500766

[51] Int. Cl.$^2$ ............................................. C07C 41/00
[52] U.S. Cl. ............................ 260/614 R; 260/611 A; 260/615 R; 260/2.5 B; 260/2.5 FP; 260/45.7 R
[58] Field of Search ............ 260/611 A, 614 R, 615 R

[56]                References Cited
            U.S. PATENT DOCUMENTS

| 1,932,590 | 10/1933 | Kaselitz ............................. 260/660 |
| 2,268,415 | 12/1941 | Morway et al. ....................... 260/23 |
| 2,464,758 | 3/1949 | Williams et al. .................. 260/614 R |
| 2,921,967 | 1/1960 | Yaron .................................... 260/660 |
| 3,378,593 | 4/1968 | Jenkner et al. ....................... 260/633 |
| 3,385,900 | 5/1968 | Carpenter et al. ............... 260/615 R |
| 3,660,318 | 5/1972 | Taniuchi et al. ................ 260/615 R |
| 3,773,696 | 12/1973 | Papa et al. ................. 260/615 R UX |

OTHER PUBLICATIONS

Hickinbottom, Reactions of Organic Compounds, Longmans, Green & Co., New York, 1956, p. 23.

Primary Examiner—Howard T. Mars
Attorney, Agent, or Firm—Millen & White

[57]                ABSTRACT

Alkoxyoctadienes are brominated with bromine to alkoxytetrabromoctanes of high purity by adding the bromine to an aqueous suspension of the alkoxyoctadienes at 0°–40° C.

12 Claims, No Drawings

PROCESS FOR THE PRODUCTION OF ALKOXYTETRABROMOCTANES

BACKGROUND OF THE INVENTION

The invention relates to a process for the production of alkoxytetrabromoctanes.

Unsaturated aliphatic and/or cycloaliphatic compounds normally are brominated by the addition of bromine to the double bond at low temperatures. Due to possible side reactions, such as, for example, the splitting off of hydrogen bromide, as well as the formation of higher brominated products, the bromination is almost always conducted in inert solvents. Especially suitable as inert solvents serving as diluents for the unsaturated compounds, for facilitating the removal of the heat of reaction and for reducing the formation of by-products are halogenated hydrocarbons, e.g., chloroform, methylene chloride, fluorochlorinated hydrocarbon, petroleum ether, ether, carbon disulfide and acetic acid. However, the reaction mixtures thus-produced during the bromination of alkyl octadienyl ethers have the serious disadvantage that they are discolored even at room temperature and, after separation of the solvent, only highly discolored products can be obtained. These highly discolored products can be purified by distillation under a high vacuum but associated with this purification operation is a rather large loss in the yield. Also, technically expensive devices are necessary and render the products, which are used as intermediates for the chemical industry, as well as flame retardants in thermoplastics, especially in expandable styrene polymers, substantially more expensive.

The reaction known as hydroxybromination of unsaturated compounds with bromine in water or with mixtures of bromine and water produces, depending on the reaction conditions, predominately or exclusively bromohydrins by the simultaneous chemical addition of a bromine cation and a hydroxy group to the double bond. See Houben-Weyl, "Methoden der organischen Chemie" V/4: 133-139, Stuttgart 1960. Additional examples of a hydrobromination can be found in German Unexamined Laid-Open Application DOS No. 1,804,804, Examples 1-4. Thus, it is possible to introduce only half of the bromine atoms into the compound possible with organic solvent bromination and an entirely different class of compounds is produced.

It is an object of this invention to provide a process for the production of alkoxytetrabromoctanes in the pure form, without appreciable proportions of colored impurities, with only minor technical and apparatus expenditures.

SUMMARY OF THE INVENTION

According to this invention, alkoxytetrabromoctanes are produced in pure form by the bromination of an aqueous suspension of the corresponding alkyl octadienyl ethers at a temperature of 0° C. to 40° C.

DETAILED DISCUSSION

In general, for economic reasons, bromine is added to the aqueous suspension of the starting alkyl octadienyl ether either dropwise, undiluted in elemental form or in the gaseous phase dissolved in an inert gas stream, until the stoichiometric quantity of bromine required for the reaction has been added. The amount of bromine employed is that required for the bromination of the double bonds, i.e., two molar equivalents if the octadiene double bonds are the only brominatable double bonds in the molecule. The amount of bromine required for complete bromination obviously must be correspondingly increased if, in addition to the octadienyl residue, there are other unsaturated residues in the molecule to which bromine adds to the double bond thereof under the reaction conditions. It is possible, though generally not particularly advantageous, to add the bromine in the form of bromine water or a mixture of bromine and bromine water. The bromine can even be in the form of a bromine-yielding compound, e.g., N-bromosuccinimide, which form is a contemplated equivalent of the bromine employed in the process of this invention. The weight ratio of bromine to the amount of water can vary over a wide range, e.g., from 1:10 to 8:10. It is possible to operate at weight ratios below 1:10, but this is not advantageous, inasmuch as the larger amount of water offers no advantages whatever and only causes additional expenses since the apparatus must be enlarged unnecessarily. A bromine to water weight ratio above 4:1 should not be employed, because an insufficient amount of water is present to dilute the alkoxyoctadienes and an accurate control of the reaction temperature at reasonable reaction times becomes difficult. Besides, undesired side reactions can occur at higher weight ratios.

The temperature range for the bromination is from 0° C. to 40° C. Below 0° C., the uniform mixing of the reaction mixture can be impeded by crystallization of the water, and above 40° C. there is the danger of side and secondary reactions in this strongly exothermic reaction. The range of 20°–30° C. is especially advantageous since in this temperature zone the heat of reaction can readily be removed with technically simple cooling systems and local hot spots can be avoided.

It is advantageous to provide the reaction mixture with up to about 10% by weight of the water thereof of an alkaline or neutral mineral salt. In general, only very minor mineral salt contents, e.g., about 0.5-2% by weight, are sufficient. Above 10% by weight, the separation of the reaction product from the aqueous phase becomes difficult. Suitable mineral salts are all salts well soluble in water and/or those less readily soluble salts which remain, after the reaction, substantially in the aqueous phase.

Examples of suitable salts are alkali metal carbonates, e.g., sodium and potassium carbonate, sodium and potassium bicarbonate, alkaline earth carbonates, e.g., magnesium and calcium carbonate, ammonium carbonate, alkali or alkaline earth acetates, alkali metal and alkaline earth halogenides, e.g., sodium chloride, potassium chloride, magnesium bromide, sodium bromide, alkali metal sulfate, magnesium sulfate, alkali metal and alkaline earth nitrates. Especially advantageous are alkali metal carbonates, particularly sodium carbonate. By the addition of the alkaline mineral salts, it is possible to achieve in a simple separation a reaction product of improved stability.

In general, any octadienyl ether which is liquid at the reaction temperature of the bromination can be used, either by itself or in a mixture with other octadienyl ethers.

Especially suitable are methyl octadienyl ethers wherein the octadienyl group, which preferably is octadien-(2,7)-yl, can be substituted by up to two methyl groups and wherein the methyl group is substituted by, in total, up to two of: alkyl of up to 7 carbon atoms, alkenyl of up to 7 carbon atoms, hydroxyalkyl of up to 3 carbon atoms, alkyloxyalkyl of 2-7 carbon atoms, alkenoxyalkyl of 3-9 carbon atoms, alkadienoxyalkyl of 5-9 carbon atoms; phenyl or toluyl and the corresponding aryl groups bearing up to 3 methyl or ethyl groups or up to 5 chlorine and/or bromine atoms. Examples of such ethers are alkoxyoctadienes of 1-4 carbon atoms in the alkoxy group, e.g. methoxyoctadienes, ethoxyoctadienes, propoxyoctadienes, butoxyoctadienes, the corresponding unsaturated hydrocarbon ethers, e.g., allyloxyoctadienes, the corresponding bis alkyl ethers, e.g., 1,2-bis[octadien-(2,7)-oxy]ethane, and and the corresponding hydrocarbon aryl and aralkyl ethers, e.g., 1-(2-phenylethoxy)-octadiene and benzoxyoctadienes, the corresponding substituted alkyl ethers, e.g., 1-(hydroxyethoxy)-octadiene and 3-(hydroxyethoxy)-octadiene, and the corresponding ethers of alkyl-substituted octadienes, e.g., alkoxy-2,6-dimethyloctadienes and alkoxy-2,7-dimethyloctadienes. In the Examples, hereinafter, the octadienyl ethers are octadien-(2,7)-yl ethers, except examples 3 and 10 wherein mixtures of octadien-(2,7)-yl- and octadien-(1,7)-yl-ethers are used.

After the reaction is complete, as evidenced by a persistent bromine color, the thus-formed product can readily be separated from the reaction mixture by decanting or centrifuging. The unpurified product is colorless and can, if necessary, be freed of acidic components by washing with water or with an aqueous solution of alkaline salt.

The thus-obtained tetrabromoctyl ethers are excellently suitable as flameproofing agents for thermoplastics, particularly for expandable styrene polymers.

The thus-obtained products contain minor amounts of water, for example, up to about 2%. However, in contrast to the bromine compounds produced conventionally in inert solvents they are so pure that they are usable directly in unpurified form as flameproofing agents for thermoplastics, especially styrene polymers. Surprisingly, it has been found that the minor water content of the crude products does not interfere with their use as flameproofing agents and, in fact, facilitates their distribution on the polymer.

The advantages attainable by the process of invention are the use of an economical reaction medium from which the reaction products can be readily separated and by the production of products which are so clean that, even without special purification operations, they can be utilized directly as flameproofing agents for thermoplastics.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

If small amounts of octadienylethers are reacted with bromine in most cases cooling of the reaction mixture during the reaction is not required. However, if large amounts of octadienylethers are reacted with bromine cooling may be necessary.

EXAMPLE 1

19.25 kg. (125 moles) of 1-ethoxyoctadiene was suspended in 75 kg. of an 0.5% aqueous soda solution. With vigorous agitation, 40 kg. (250 moles) of liquid bromine was added dropwise thereto within 5 hours. The temperature rose from 22° C to 29° C. during the dropwise addition and was held at this temperature by cooling. After the addition was complete and the reaction had ended, the aqueous phase was separated and the reaction product washed twice with 50 l. portions of 0.5% soda solution and once with 75 l. of water. The tetrabrominated 1-ethoxyoctadiene, obtained as a colorless liquid showing a milky turbidity, was separated. Yield: 53 kg. The product contained 0.57% water and had a bromine content of 64-65%.

EXAMPLE 2

462 g. of 1-ethoxyoctadiene was suspended in 1,800 g. of 0.5% aqueous soda solution and reacted with 960 g. of liquid bromine. The reaction temperature was 20°-25° C. The bromine was added dropwise within 4-5 hours, whereupon the reaction mixture was stirred for another 2 hours.

The reaction product was separated from the aqueous phase and washed with aqueous soda solution and water, thus isolating 1,044 g. of a colorless liquid. The bromine content was 67%.

EXAMPLE 3

The procedure of Example 2 was followed, but replacing the 1-ethoxyoctadiene by a mixture of 83 parts by weight of 1-ethoxyoctadiene and 17 parts by weight of 3-ethoxyoctadiene. Yield: 1,254 g. of a colorless, turbid liquid having a bromine content of 67.5%.

EXAMPLE 4

At 20°-25° C. and under vigorous agitation, 960 g. (6 moles) of liquid bromine was added dropwise within 5 hours to a mixture of 335 g. (2 moles) of 1-allyloxyoctadiene and 1,200 g. of 1% aqueous soda solution. The reaction mixture was then stirred for another 2 hours. Thereafter, the reaction product was separated from the aqueous phase and washed with soda solution and water, yielding 1,250 g. of a colorless, turbid liquid having a bromine content of about 62% and a water content of 14%. By centrifuging (4,400 r.p.m.), the largest part of the water was separated from the crude product. The colorless, turbid product still contained 2% of water and had a bromine content of 72%.

EXAMPLE 5

Similarly as in Example 4, 219 g. of 1-butoxyoctadiene was reacted in 720 g. of 1% potassium bicarbonate solution with 384 g. of liquid bromine, and the reaction mixture was worked up, yielding 520 g. (86.3%) of a colorless liquid having a bromine content of 61%.

EXAMPLE 6

78 g. of 1-ethoxyoctadiene was suspended in 300 g. of water and reacted as described above with 160 g. of liquid bromine within 1 hour at a temperature of 20°-25° C. The reaction mixture was then stirred for another 2 hours at room temperature. Then, the aqueous phase was separated, and the reaction product was washed with water, yielding 210 g. of a liquid of milky turbidity having a bromine content of 64.5%.

EXAMPLE 7

39 g. of 1-ethoxyoctadiene was reacted as described in Example 6 with 80 g. of liquid bromine in 150 g. of a 5% aqueous sodium carbonate solution and worked up analogously. Yield: 97 g. of a colorless, turbid liquid having a bromine content of 64%.

EXAMPLE 8

39 g. of 1-ethoxyoctadiene was reacted in accordance with Example 6 with 80 g. of liquid bromine in 150 g. of a 1% sodium chloride solution and then worked up. The reaction product was washed with 0.5% soda solution and water, yielding 99 g. of a liquid having a bromine content of between 64% and 65%.

EXAMPLE 9

A suspension was prepared from 426 g. of 1-(2-hydroxyethoxy)-octadiene and 800 g. of a 1% aqueous sodium carbonate solution. Within 5 hours, 800 g. of liquid bromine was added at room temperature, during which the temperature rose to 26° C. The reaction mixture was further stirred for 2 hours at room temperature and then the aqueous phase was separated. The reaction product was washed twice with 0.5% sodium carbonate solution and once with water and then separated, thus obtaining 1,047 g. of a liquid of milky turbidity with a water content of 1.89% and a bromine content of 61%.

EXAMPLE 10

Following the procedure of example 2 164 g of a mixture of 73 parts by weight of 1-ethoxy-2,6-dimethyloctadiene-(2,7) and 27 parts by weight of 3-ethoxy-2,6-dimethyloctadiene-(1,7) were reacted with 288 g of liquid bromine. Yield: 305 g of a colorless turbid liquid having a bromine content of 59%.

EXAMPLE 11

Following the procedure of example 2 195 g of 1,2-bis[octadiene-(2,7)-yloxy]ethane was reacted with 448 g of liquid bromine. Yield: 680 g of a colorless viscous paste having a bromine content of 56%.

By centrifugating (4,000 r.p.m.) the largest part of the remaining water was separated giving a product having a bromine content of 65%.

EXAMPLE 12

24 g of 1-(2-ethylhexoxy-)octadiene was suspended in 100 ml of 0,5% sodium carbonate solution and reacted with 32 g of liquid bromine following the procedure of example 2. Yield: 54 g of a colorless turbid liquid of a bromine content of 52%.

EXAMPLE 13

Following the procedure of example 12 18 g of 1-(2-hydroxy-propoxy-)octadiene was reacted with 34 g of liquid bromine. Yield: 34 g of a colorless turbid liquid with a bromine content of 58%.

EXAMPLE 14

29 g of 1,2-bis(octadiene-2,7-yloxy-)propane was suspended in 100 ml of 0,5% sodium carbonate solution. Within 2 hours 66 g of liquid bromine was added dropwise. The reaction temperature rose to 28° C, cooling was not necessary. The reaction mixture was then stirred for another 3 hours. Thereafter the reaction product was seperated from the aqueous phase and washed with water, yielding 106 g of a colorless liquid with a water content of about 10%. By centrifuging (4,400 r.p.m.) 20 g of said liquid another 2 g of water could be separated giving a colorless viscous paste with a bromine content of 55%.

EXAMPLE 15

Following the procedure of example 14 37 g of the bis-(octadienyl-)ether of triglycol was reacted with 66 g of liquid bromine yielding 76 g of a colorless viscous paste with a bromine content of 54%.

EXAMPLE 16

(Comparative Example)

Bromination of 1-ethoxyoctadiene-(2,7) in methanol, 308 g of 1-ethoxyoctadiene-(2,7) was dissolved in 1,000 ml of methanol. The solution was cooled to $-10°$ to $-20°$ C and with vigorous agitation 640 g of liquid bromine was added dropwise within 3 hours at this temperature. After the addition was complete the reaction mixture was stirred for another 3 hours at room temperature. Two phases occurred within the reaction mixture which were separated. The lower phase consisting substantially of 1-ethoxytetrabromooctane was dissolved in ether and washed several times with water. The ether was evaporated by means of a rotational evaporator. Yield: 462 g of a dark colored fluid with a bromine content of 59%. The methanolic phase was treated in a rotational evaporator to evaporate the methanol. The remaining red-brown colored liquid was dissolved in ether and washed several times with water. After evaporating the ether the yield was 378 g of a dark-brown liquid having a bromine content of 59%. 60 g of the crude product were fractionated under vacuum $(2 \cdot 10^{-3}$ mbar) yielding 41 g of a yellowish fluid with a bromine content of 61%.

EXAMPLE 17

To show the flame-proofing ability of 1-ethoxytetrabromooctane manufactured in different ways styrene polymer in bead forms containing a blowing agent was impregnated (under pressure) with 1-ethoxytetrabromooctane manufactured in different ways in a solution of 1% polyvinylalcohol (molecular weight) in water at a temperature of 100° C. After impregnating the pellets were washed with water and dried. Perforated metal moulds (30 × 30 × 100 mm) were filled with 6 g of the polystyrene beads obtained and then treated in boiling water. The resulting test specimens were dried and examined for their burning behaviour by the following test: The test specimens are clamped vertically in a holder and the specimens are ignited with an approx. 3 cm high non-luminous Bunsen burner flame until the material burns (3 to 4 seconds). Afte removing the flame, the smouldering time in seconds is measured and used for comparison. The table which follows contrasts the results of the flame test of expanded polystyrene test-specimens in which were incorporated 1-ethoxytetrabromooctane made in example 1 (following the invention) and 1-ethoxytetrabromooctanes made in comparative example 16.

| bromine compound | Color | test - specimen bromine content of the polymer, % by weight | smouldering time (sec.) |
|---|---|---|---|
| 1-ethoxytetrabromo-octane following the invention (example 1) | colorless | 1.05 | 5; 8 |
|  |  | 0.52 | 7; 15; 11; 6 |
| 1-ethoxytetrabromo-octane | yellowish | 1.12 | 13; 11; |

-continued

| bromine compound | test - specimen | | |
|---|---|---|---|
| | Color | bromine content of the polymer, % by weight | smouldering time (sec.) |
| (comparative example 16) 1-ethoxytetra-bromo-octane | | | 9; 17 |
| (comparative example 16, distilled) | colorless | 1.16 | 10; 6 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the tetrabromination with bromine of a liquid octadienyl ether to produce the corresponding tetrabromooctane ether, the improvement which comprises adding the bromine to an aqueous suspension of the liquid octadienyl ether at 0° C. to 40° C. and wherein the aqueous suspension contains up to 10% by weight of an alkaline or neutral mineral salt, based on the water.

2. A process according to claim 1, wherein the bromination is conducted at 20°-30° C.

3. A process according to claim 1, wherein the bromine is added as liquid bromine.

4. A process according to claim 1, wherein the octadienyl ether is selected from the group consisting of methoxyoctadienes, ethoxyoctadienes, propoxyoctadienes, and butoxyoctadienes.

5. A process according to claim 1, wherein the octadienyl ether is ethoxyoctadiene.

6. A process according to claim 1, wherein the mineral salt is sodium carbonate.

7. A process according to claim 1, wherein the octadienyl ether is selected from the group consisting of methoxyoctadienes, ethoxyoctadienes, propoxyoctadienes, and butoxyoctadienes and wherein the bromine is added as liquid bromine at a temperature of 20°-30° C.

8. A process according to claim 7, wherein the aqueous suspension contains 0.5-2% of sodium carbonate.

9. A process according to claim 8, wherein the octadienyl ether is ethoxyoctadiene.

10. A process for the production of colorless, plastic flameproofing grade alkoxytetrabromoctane of 1-4 carbon atoms in the alkoxy group with a bromine content of at least 61%, consisting essentially of the steps of (a) reacting a corresponding alkoxyoctadiene with bromine according to the process of claim 1; and (b) separating the thus-produced 1-alkoxytetrabromoctane from the reaction mixture by decanting or centrifuging.

11. A process according to claim 10 wherein the alkoxyoctadiene is ethoxyoctadiene and the bromine is added as liquid bromine at a temperature of 20°-30° C.

12. A process according to claim 11 wherein the mineral salt is an alkali metal carbonate.

* * * * *